United States Patent
Cavalla et al.

(10) Patent No.: US 7,470,690 B2
(45) Date of Patent: Dec. 30, 2008

(54) 4-(2-FLUOROPHENYL)-6-METHYL-2-(1-PIPERAZINYL)THIENO[2,3-D] PYRIMIDINE IN THE TREATMENT OF FUNCTIONAL BOWEL DISORDER

(75) Inventors: David Cavalla, Cambridge (GB); Robert William Gristwood, Cambridge (GB)

(73) Assignee: Dynogen Pharmaceuticals, Inc., Waltham, MA (US)

( * ) Notice: Subject to any disclaimer, the term of this patent is extended or adjusted under 35 U.S.C. 154(b) by 171 days.

(21) Appl. No.: 10/519,594

(22) PCT Filed: Jul. 9, 2003

(86) PCT No.: PCT/GB03/02974

§ 371 (c)(1),
(2), (4) Date: Dec. 28, 2004

(87) PCT Pub. No.: WO2004/004734

PCT Pub. Date: Jan. 15, 2004

(65) Prior Publication Data

US 2005/0239792 A1    Oct. 27, 2005

(30) Foreign Application Priority Data

Jul. 10, 2002 (GB) ................. 0216027.3
Feb. 23, 2003 (GB) ................. 0304648.9

(51) Int. Cl.
*A61K 31/497* (2006.01)
*C07D 471/04* (2006.01)
*C07D 237/00* (2006.01)
*A01N 43/54* (2006.01)

(52) U.S. Cl. .............. 514/252.16; 514/257; 514/267; 544/239

(58) Field of Classification Search ............ None
See application file for complete search history.

(56) References Cited

U.S. PATENT DOCUMENTS

| | | | |
|---|---|---|---|
| 4,695,568 A | 9/1987 | Ninomiya et al. | |
| 4,845,092 A | 7/1989 | Sanger et al. | |
| 4,939,136 A | 7/1990 | Haeck et al. | |
| 5,225,407 A | 7/1993 | Oakley et al. | |
| 5,352,685 A | 10/1994 | Maruyama et al. | |
| 5,434,174 A | 7/1995 | Gidda et al. | |
| 5,438,068 A | 8/1995 | Eeckhout et al. | |
| 5,470,868 A | 11/1995 | Young | |
| 5,530,008 A | 6/1996 | Azcona et al. | |
| 5,576,317 A | 11/1996 | Gonsalves | |
| 5,663,343 A | 9/1997 | van der Meij et al. | |
| 5,708,033 A | 1/1998 | Kelley et al. | |
| 5,945,415 A | 8/1999 | Kato et al. | |
| 5,962,494 A | 10/1999 | Young | |
| 5,977,127 A | 11/1999 | Bonnacker et al. | |
| 5,977,175 A | 11/1999 | Lin | |
| 5,985,866 A | 11/1999 | Müuller et al. | |
| 5,990,159 A | 11/1999 | Meulemans et al. | |
| 6,008,227 A * | 12/1999 | Davies et al. ............ | 514/304 |
| 6,054,461 A | 4/2000 | Fairbanks et al. | |
| 6,117,879 A | 9/2000 | Fairbanks et al. | |
| 6,156,771 A | 12/2000 | Rubin et al. | |
| 6,194,382 B1 | 2/2001 | Crain et al. | |
| 6,211,171 B1 | 4/2001 | Sawynok et al. | |
| 6,235,745 B1 | 5/2001 | Megens | |
| 6,284,770 B1 | 9/2001 | Mangel et al. | |
| 6,300,336 B1 | 10/2001 | Eeckhout et al. | |
| 6,303,613 B1 * | 10/2001 | McInally et al. ......... | 514/260.1 |
| 6,355,647 B1 | 3/2002 | Steiner et al. | |
| 6,384,042 B2 | 5/2002 | Färber et al. | |
| 6,429,209 B2 | 8/2002 | Mangel et al. | |
| 6,440,453 B1 | 8/2002 | Fischer et al. | |
| 6,441,038 B1 | 8/2002 | Loder et al. | |
| 6,458,795 B1 | 10/2002 | Bergeron, Jr. | |
| 6,465,458 B1 | 10/2002 | Wong et al. | |
| 6,476,078 B1 | 11/2002 | Jerussi et al. | |
| 6,558,708 B1 | 5/2003 | Lin | |
| 6,566,369 B2 | 5/2003 | Cautreels et al. | |
| 6,593,336 B2 | 7/2003 | Mangel et al. | |
| 7,094,786 B2 | 8/2006 | Landau | |
| 7,220,748 B2 | 5/2007 | Cavalla et al. | |
| 2001/0020025 A1 | 9/2001 | Megens | |
| 2001/0044450 A1 | 11/2001 | Mangel et al. | |

(Continued)

FOREIGN PATENT DOCUMENTS

CA    2431074    6/2002

(Continued)

OTHER PUBLICATIONS

Wu et al. (Effects of Acute and Chronic Administration of MCI-225, a New Selective Noradrenaline Reuptake Inhibitor With 5-HT3 Receptor Blocking Action, on Extracellular Noradrenaline Levels in the Hypothalamus of Stressed Rats. 2000. Japan. Journal of Pharmacology.83.pp. 31-38).*

(Continued)

*Primary Examiner*—Sreeni Padmanabhan
*Assistant Examiner*—Layla Soroush
(74) *Attorney, Agent, or Firm*—Hamilton, Brook, Smith & Reynolds, P.C.

(57) ABSTRACT

Use of 4-(2-Fluorophenyl)-6-Methyl-2-(1-Piperazinyl) Thieno[2,3-D]Pyrimidine or a salt thereof for the manufacture of a medicament for the treatment of functional bowel disorder.

3 Claims, No Drawings

U.S. PATENT DOCUMENTS

| | | |
|---|---|---|
| 2001/0056110 A1 | 12/2001 | Faerber et al. |
| 2002/0002197 A1 | 1/2002 | Mueller et al. |
| 2002/0039599 A1 | 4/2002 | Lin et al. |
| 2002/0040033 A1 | 4/2002 | Cautreels et al. |
| 2002/0086880 A1 | 7/2002 | Rubin et al. |
| 2002/0086881 A1 | 7/2002 | Rubin et al. |
| 2002/0107244 A1 | 8/2002 | Howard, Jr. |
| 2003/0036549 A1 | 2/2003 | Mangel et al. |
| 2003/0125349 A1 | 7/2003 | Cautreels et al. |
| 2003/0158221 A1 | 8/2003 | Zhang et al. |
| 2003/0203055 A1 | 10/2003 | Rao et al. |
| 2004/0048874 A1 | 3/2004 | Bardsley |
| 2004/0147509 A1 | 7/2004 | Landau |
| 2004/0147510 A1 | 7/2004 | Landau |
| 2004/0254168 A1 | 12/2004 | Landau |
| 2004/0254169 A1 | 12/2004 | Landau |
| 2004/0254170 A1 | 12/2004 | Landau |
| 2004/0254171 A1 | 12/2004 | Landau et al. |
| 2004/0254172 A1 | 12/2004 | Landau et al. |
| 2004/0259862 A1 | 12/2004 | Landau |
| 2005/0032780 A1 | 2/2005 | Landau |
| 2005/0192270 A1 | 9/2005 | Landau |
| 2005/0239792 A1 | 10/2005 | Cavalla et al. |
| 2006/0167005 A1 | 7/2006 | Cavalla et al. |
| 2006/0217391 A1 | 9/2006 | Landau |

FOREIGN PATENT DOCUMENTS

| | | |
|---|---|---|
| DE | 100 63 223 | 6/2002 |
| EP | 0150469 | 6/1988 |
| EP | 0 297 651 B1 | 11/1993 |
| EP | 1 230 921 A1 | 8/2002 |
| WO | WO 88/04173 | 6/1988 |
| WO | WO 94/01095 | 1/1994 |
| WO | WO 96/11009 | 4/1996 |
| WO | WO 98/01157 | 1/1998 |
| WO | WO 98/08520 | 3/1998 |
| WO | WO 98/09623 | 3/1998 |
| WO | WO 98/50037 | 11/1998 |
| WO | WO 00/48581 A3 | 8/2000 |
| WO | WO 00/48597 | 8/2000 |
| WO | WO 00/51583 | 9/2000 |
| WO | WO 00/51584 | 9/2000 |
| WO | WO 01/26623 A2 | 4/2001 |
| WO | WO 01/26623 A3 | 4/2001 |
| WO | WO 02/07713 A2 | 1/2002 |
| WO | WO 02/083926 A2 | 10/2002 |
| WO | WO 02/083926 A3 | 10/2002 |
| WO | WO 02/094249 A1 | 11/2002 |
| WO | WO 03/061657 A1 | 7/2003 |
| WO | WO 03/063873 A1 | 8/2003 |
| WO | WO 03/077897 A1 | 9/2003 |
| WO | WO 2004/004734 A1 | 1/2004 |
| WO | WO 2004/019948 A1 | 3/2004 |
| WO | WO 2004/058353 A2 | 7/2004 |
| WO | WO 2004/058353 A3 | 7/2004 |
| WO | WO 2004/062623 A2 | 7/2004 |
| WO | WO 2004/062624 A2 | 7/2004 |
| WO | WO 2004/062624 A3 | 7/2004 |

OTHER PUBLICATIONS

Crowell M. D., "The Role of Serotonin in the Pathophysiology of Irritable Bowel Syndrome," *American Journal of Managed Care*, 2001, 7:S252-S260.

Eguchi J. et al., "The Anxiolytic-like Effect of MCI-225, a Selective NA Reuptake Inhibitor With 5-HT3 Receptor Antagonism," *Pharmacology, Biochemistry and Behavior*, 2000, 68:677-683.

"How to Avoid a Health Insurance Claim Denial- and What to do When You Can't," [Retrieved on Mar. 15, 2005]. Retrieved from the Internet <URL:http://info.insure.com/health/claimdenial.html>, pp. 1-4.

Irritable Bowel Syndrome at a Glance—Nosology, Epidemiology, and Pathophysiology (Monograph I), Dec. 2002 [Retrieved on Dec. 12, 2002]. Retrieved from the Internet <URL:http://fdhn.org/html/education/gi/ibs_nosology.htm>, pp. 1-2.

"Dynogen Pharmaceuticals, Inc. Enters Into Agreement With Mitsubishi Pharma For Irritable Bowel Syndrome Compound," Dynogen Pharmaceuticals, Inc. Press Release, pp. 1-2 [online], (Dec. 22, 2003). Retrieved from the Internet <URL: www.dynogen.com>.

Angel, I., et al. "Litoxetine: A Selective 5-HT Uptake Inhibitor with Concomitant 5-HT$_3$ Receptor Antagonist and Antiemetic Properties," *Eur. J. Pharmacol.*, 232(2/3):139-145 (1993).

Béïque, J.C., et al., "Affinities of Venlafaxine and Various Reuptake Inhibitors for the Serotonin and Norepinephrine Transporters," *Eur. J. Pharmacol.*, 349(1):129-132 (1998).

Burns, M.J., "The Pharmacology and Toxicology of Reboxetine," *Int. J. Med. Toxicol.* 3(4):26 1-7 (2000).

Bymaster, F.P., et al. "Comparative Affinity of Duloxetine and Venlafaxine for Serotonin and Norepinephrine Transporters in vitro and in vivo, Human Serotonin Receptor Subtypes, and Other Neuronal Receptors," *Neuropsychopharmacology*, 25(6):871-880 (2001).

Camilleri, M., "Serotonergic Drugs: Emerging Therapies for Irritable Bowel Syndrome," In Irritable Bowel Syndrome a Clinician's Guide, M. Camilleri and R. C. Spiller, eds., Chapt. 19; pp. 1-10 (2002).

Camilleri, M., "Serotonergic Modulation of Visceral Sensation: Lower Gut," *Gut 51*(Supp. 1):i81-i86 (2002).

Center for Drug Evaluation and Research Application No. 020623; Pharmacology Reviews; Jul. 5, 1996, pp. 1-40.

Database CIN Jan. 5, 2004, "Life Sciences in Brief," [online], (retrieved online Jan. 31, 2006). Retrieved from: STN Database, Accession No. 33(3):1518T.

Database IMSDRUGNEWS, R&D Focus Drug News, "DDP 225 Dynogen, Mitsubishi Pharma Licensing Agreement," [online], Jan. 12, 2004. Retrieved from: STN Database, Accession No. 2004:188.

Depoortere, I., et al., "Dose-Dependent Effects of Recombinant Human Interleukin-11 on Contractile Properties in Rabbit 2,4,6-Trinitrobenzene Sulfonic Acid Colitis," *J. Pharmacol. Exp. Ther.*, 294(3): 983-990 (2000).

Drossman, D.A., et al., "Irritable Bowel Syndrome: A Technical Review for Practice Guideline Development," *Gastroenterology*, 112: 2120-2137 (1997).

Eguchi, J., et al., "Pharmacological Profile of the Novel Antidepressant 4-(2-Fluorophenyl)-6-methyl-2-(1-piperazinyl)thieno-[2,3-d]pyrimidine Monohydrate Hydrochloride," *Arzneim.-Forsch./Drug Res.*, 47(12): 1337-1347 (1997).

Fairweather, D.B., et al., "The Psychomotor and Cognitive Effects of Litoxetine in Young and Middle Aged Volunteers," *Br. J. Clin. Pharmacol.*, 40(2):119-125 (1995).

Gebhart, G.F., "Pathobiology of Visceral Pain: Molecular Mechanisms and Therapeutic Implications IV. Visceral Afferent Contributions to the Pathobiology of Visceral Pain," *Am. J. Physiol. Gastrointest. Liver Physiol.* 278:G834-G838 (2000).

Goldberg, P.A., et al., "Modification of Visceral Sensitivity and Pain in Irritable Bowel Syndrome by 5-HT$_3$ Antagonism (Ondansetron)," *Digestion*, 57(6):478-483 (1996).

Greenbaum, D.S., et al., "Effects of Desipramine on Irritable Bowel Syndrome Compared with Atropine and Placebo," *Digestive Diseases and Sciences*, 32(3): 257-266 (1987).

Ishigooka, Jr., et al., "Serotonin-Noradrenaline Reuptake Inhibitors(SNRIs)," *Nippon Rinsho*, 59, pp. 1523-1529, (2001)—Abstract Only.

Ito, C., et al., "Effect of GK-128 [2-[(2-Methylimidazol-1-yl)methyl]-benzo[f]thiochromen-1-one Monohydrochloride Hemihydrate], a Selective 5-Hydroxytryptamine$_3$ Receptor Antagonist, on Colonic Function in Rats," *J. Pharmacol. Exp. Ther.*, 280(1): 67-72 (1997).

Jin, J.G., et al., "Propulsion in Guinea Pig Colon Induced by 5-Hydroxytryptamine (HT) via 5-HT$_4$ and 5-HT$_3$ Receptors," *J. Pharmacol. Exp. Ther.*, 288(1): 93-97 (1999).

Kozlowski, C.M., et al., "The 5-HT$_3$ Receptor Antagonist Alosetron Inhibits the Colorectal Distention Induced Depressor Response and Spinal *c-fos* Expression in the Anaesthetised Rat," *Gut*, 46: 474-480 (2000).

Lotronex—Tablets, Product Information, GlaxoSmithKline, Research Triangle Park, NC, pp. 1-13 (2002).

Mertz, H.R., "Irritable Bowel Syndrome," *N. Engl. J. Med.* 349(22):2136-2146 (2003).

Million, M., et al., "Susceptibility of Lewis and Fischer Rats to Stress-induced Worsening of TNB-colitis: Protective Role of Brain CRF," *Amer. Phys. Soc.*, 276 (4 Pt 1): G1027-G1036 (1999).

Morteau, O., et al., "Influence of 5-$HT_3$ Receptor Antagonists in Visceromotor and Nociceptive Responses to Rectal Distension Before and During Experimental Colitis In Rats," *Fundam. Clin. Pharmacol.*, 8(6):553-562 (1994).

Owens, M. J., et al., "Neurotransmitter Receptor and Transporter Binding Profile of Antidepressants and their Metabolites," *J. Pharmacol. Exp. Ther.*, 283(3): 1305-1322 (1997).

Sach, J.A., et al., "Irritable Bowel Syndrome," *Curr. Treat. Options. Gastroenterol.*, 5(4): 267-278 (2002).

Schmulson, M.J., "Brain-Gut Interaction in Irritable Bowel Syndrome: New Findings of a Multicomponent Disease Model," *IMAJ*, 3:104-110 (2001).

Sheikh, M. Y. and Wright, R.A., "Irritable Bowel Syndrome: Current Concepts and Future Prospects," *Hospital Physician*, pp. 31-38 (1999).

Spiller, R., "Pharmacotherapy: Non-Serotonergic Mechanisms," *Gut*, 51, Suppl, i87-i90 (2002).

Steadman, C.J., et al., "Selective 5-Hydroxytryptamine Type 3 Receptor Antagonism With Ondansetron as Treatment for Diarrhea-Predominant Irritable Bowel Syndrome: A Pilot Study," *Mayo Clinic Proc.*, 67(8): 732-738 (1992).

Thompson, W.G., et al., "Functional Bowel Disorders and Functional Abdominal Pain," *Gut* 45(Supp II):1143-1147 (1999).

U.S. Appl. No. 60/364,531, filed Mar. 15, 2002, entitled "Methods of Treating Visceral Pain Syndromes," by Rao et al., priority document for WO 03/077897 A1 and U.S. 2003/0203055 A1.

Venkova, K., et al., "Peripheral Activity of a New $NK_1$ Receptor Antagonist TAK-637 in the Gastrointestinal Tract," *J. Pharmacol. Exp. Ther.*, 300(3): 1046-1052 (2002).

Wong, E.H.F., et al., "Reboxetine: A Pharmacologically Potent, Selective, and Specific Norepinephrine Reuptake Inhibitor," *Biol. Psychiatry.* 47(9): 818-829 (2000).

Wood, J.D., et al. "Fundamentals of Neurogastroenterology," *Gut* 45(Supp. II):II6-III6 (1999).

Worsley, A.P. and Allawi, J., "A Combined Treatment for Severe Diabetic Neuropathy Symptoms," in *Letters, Diabetic Medicine*, 15:797-798 (1998).

Yuan, S.Y., et al., "Investigation of the Role of 5-$HT_3$ and 5-$HT_4$ Receptors in Ascending and Descending Reflexes to the Circular Muscle of Guinea-pig Small Intestine," *Br. J. Pharmacol.*, 112(4): 1095-1100 (1994).

* cited by examiner

4-(2-FLUOROPHENYL)-6-METHYL-2-(1-PIPERAZINYL)THIENO[2,3-D]PYRIMIDINE IN THE TREATMENT OF FUNCTIONAL BOWEL DISORDER

This applicacion is a National Stage Application of International Application Number PCT/GB03/02974, filed Jul. 09, 2003; which claims priority to United Kingdom Application No. 0216027.3 , filed Jul. 10, 2002 and United Kingdom Application No. 0304648.9, filed Feb. 28, 2003.

FIELD OF THE INVENTION

This invention relates to a new use for a known compound.

BACKGROUND OF THE INVENTION 4-(2-Fluorophenyl)-6-methyl-2-(1-piperazinyl)thieno[2,3-D]pyrimidine monohydrate hydrochloride is known (see U.S. Pat. No. 4,695,568) and has shown activity as an antidepressant. It has serotonin and noradrenergic reuptake blocking properties and this is thought to be the mechanism for its action as an antidepressant. The compound also has 5HT-3 blocking activity.

Functional bowel disorders are very common and include irritable bowel syndrome (IBS) and functional dyspepsia. IBS is the most common disorder diagnosed by gastroenterologists and one of the more common encountered in general practice. The overall prevalence rate is similar (approx 10%) in most industrialised countries. Some estimates of prevalence have reached 20%. The illness has a large economic impact on health care use and indirect costs, chiefly through absenteeism.

IBS falls into two categories of equal prevalence, constipation-predominant and diarrhoea-predominant. The available treatments are generally poor.

A recent approach to treating diarrhoea-predominant IBS has involved the use of alosetron. This drug works by blocking the 5HT-3 receptor. Other drugs with this mechanism of action have shown some limited activity in this disease, including granisetron. Alosetron, although effective, was withdrawn due to side-effects on the colon.

A recent approach to treating constipation-predominant IBS involved agonising the 5HT4 receptor. Two such agonists are in clinical trials, i.e. tegaserod and prucalopride. Other approaches being explored include using 5HT1 agonists such as buspirone.

Functional dyspepsia is characterised by impaired accommodation of the stomach to a meal and epigastric pain discomfort or pain. There is often early satiety and weight loss. The disorder is not well understood. Treatments include antispasmodics and drugs affecting gut motility. Early studies suggest that buspirone and serotonin reuptake inhibitors may be useful.

SUMMARY OF THE INVENTION

Surprisingly, it has been found that the known compound identified above (referred to herein as MCI-225) has activity in the treatment of functional bowel disorders. Its combination of serotonin and noradrenergic reuptake blockade and 5HT-3 receptor blockade has not previously been clearly identified as being responsible for activity in functional bowel disorders. Furthermore MCI-225, at doses effective in the treatment of bowel disorders, can produce a lower incidence of some of the side-effects which are commonly known to be associated with the clinical use of selective serotonin reuptake inhibitors, for example the production of nausea and vomiting or the induction of sexual dysfunction. It will be appreciated that any suitable form of the active principle may be used, e.g. another salt form, or a prodrug or active metabolite.

DESCRIPTION OF PREFERRED EMBODIMENTS

By means of this invention, functional bowel disorders and associated pain symptoms can be treated, e.g. controlled or prevented. Such disorders include irritable bowel syndrome, including diarrhoea-predominant, constipation-predominant, and alternating constipation/diarrhoea IBS. The patient may be male or female, diarrhoea-predominant IBS being particularly associated with women.

For use in the invention, the active compound can be formulated in any suitable manner together with a conventional diluent or carrier. The active compound is preferably administered by the oral route; other suitable routes of administration include sublingual/buccal, transdermal, intramuscular, intranasal, rectal, parenteral, subcutaneous, pulmonary and topical. An effective dose of the active agent will depend on the nature and degree of the complaint, the age and condition of the patient and other factors known to those skilled in the art. A typical daily dosage may be 0.1 mg to 1 g.

A pharmaceutical composition containing the active ingredient may be in the form of a sublingual tablet or patch. Suitable compositions for oral use include tablets, troches, lozenges, aqueous or oily suspensions, dispersible powders or granules, emulsions, hard or soft capsules, syrups and elixirs. Suitable additives include sweetening agents, flavouring agents, colouring agents and preserving agents. Tablets contain the active ingredient in admixture with non-toxic pharmaceutically acceptable excipients, e.g. inert diluents such as calcium carbonate, sodium carbonate, lactose, calcium phosphate or sodium phosphate; granulating and disintegrating agents, for example corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastointestinal tract and thereby provide a sustained action over a longer period. For example, a time delay material such as glyceryl monostearate or glyceryl distearate may be employed. They may also be coated, to form osmotic therapeutic tablets for controlled release. Hard gelatin capsules may include an inert solid diluent, for example calcium carbonate, calcium phosphate or kaolin; soft gelatin capsules may include water or an oil medium, for example peanut oil, liquid paraffin or olive oil.

The data on which this invention is based will now be described. In a study using intact animals, the ability of a drug to inhibit the reflex depressor response to colorectal distension can be assessed. In this model, an inhibition of the reflex indicates modulation of visceral nociceptive neurotransmission and, therefore, the use of the drug in functional bowel disease (e.g. IBS); see Kozlowski et al, 2000, Gut 46, 474-480. Allodynia and visceral pain are important components of functional bowel disease.

Study

Experiments were performed on male Sprague-Dawley rats (250-300 g). Anaesthesia was induced with isoflurane (2.5% in oxygen) and maintained with alpha chlorolose (80 mg/kg i.v.). The left carotid artery was cannulated for the measurement of blood pressure and heart rate and the left jugular vein cannulated for drug administration. A tracheal cannula was implanted for artificial respiration if required. A 10 mm long latex balloon was inserted intrarectally so that the tip of the balloon was 20 mm from the anal verge (Kozlowski et al, supra). The balloon was connected via a double lumen cannula to a pressure transducer and also to a saline-filled syringe for inflation/deflation of the balloon. Throughout the experiment, body temperature was kept constant at 36-38 C using a homeothermic blanket.

Once stable baseline parameters were obtained (approximately after 20 minutes), the balloon was rapidly inflated with increasing volumes of saline (0.5-2.5 ml) for 30 seconds at 5 minute intervals, and the resultant change in blood pressure recorded. Three distinct response curves were constructed, with a 10 minute stabilisation period between each curve. In one group of animals, 10 minutes prior to the commencement of the final distension response curve, a single bolus of MCI-225 (3 mg/kg) was administered intravenously; in a second group of animals, a single bolus dose of vehicle was administered. The effect of MCI-225 and vehicle was determined by analysing the changes in colorectal distension that evoked depressor response.

Falls in arterial blood pressure (mean absolute decreases in mean arterial pressure in mmHg, with standard error of mean in brackets) evoked by distension of the balloon, before adding drug, at 0.5, 1.0, 1.5, 2.0 and 2.5 ml balloon volume were 2.7 (1.9), 12.4 (5.9), 24.0 (8.9), 36.3 (4.8) and 43.4 (6.0), respectively (all except final value n=6, final value n=5). Following administration of MCI-225 at 3 mg/kg i.v., the corresponding values were 2.2 (1.65), 6.3 (2.6), 10.6 (3.9), 15.3 (5.4) and 24.6 (7.3), respectively (all values except final value n=6, final value n=5).

The results clearly show that MCI-225 inhibited the distension-induced falls in blood pressure. The falls in blood pressure evoked by 2.0 and 2.5 ml balloon volumes were reduced with statistical significance following administration of MCI-225 at 3 mg/kg, with p values (paired t test) of less than 0.01 and less than 0.05 respectively.

The invention claimed is:

1. A method for the treatment of an irritable bowel syndrome selected from diarrhea-predominant irritable bowel syndrome, alternating constipation/diarrhea bowel syndrome, and constipation-predominant irritable bowel syndrome wherein said method comprises orally administering, to a patient in need of such treatment, an effective amount of 4-(2-fluorophenyl)-6-methyl-2-(1-piperazinyl)thieno [2,3-D]pyrimidine or a salt thereof.

2. The method, according to claim 1, wherein the salt is the hydrochloride monohydrate.

3. The method, according to claim 1, wherein the disorder is in a female patient.

\* \* \* \* \*

UNITED STATES PATENT AND TRADEMARK OFFICE
CERTIFICATE OF CORRECTION

PATENT NO.         : 7,470,690 B2
APPLICATION NO. : 10/519594
DATED              : December 30, 2008
INVENTOR(S)        : David Cavalla and Robert William Gristwood It is certified that error appears in the above-identified patent and that said Letters Patent is hereby corrected as shown below:

Column 4, line 16: Delete "alternating constipation/diarrhea bowel"
and insert --alternating constipation/diarrhea irritable bowel--

Signed and Sealed this

Twenty-fourth Day of March, 2009

JOHN DOLL
*Acting Director of the United States Patent and Trademark Office*